United States Patent
Liu et al.

(10) Patent No.: US 8,216,515 B2
(45) Date of Patent: Jul. 10, 2012

(54) CAPILLARY ION CHROMATOGRAPHY

(75) Inventors: Yan Liu, Palo Alto, CA (US); Victor Manuel Berber Barreto, Campbell, CA (US); Christopher A. Pohl, Union City, CA (US); Nebojsa Avdalovic, Cupertino, CA (US)

(73) Assignee: Dionex Corporation, Sunnyvale, CA (US)

( * ) Notice: Subject to any disclaimer, the term of this patent is extended or adjusted under 35 U.S.C. 154(b) by 1747 days.

(21) Appl. No.: 10/944,442

(22) Filed: Sep. 16, 2004

(65) Prior Publication Data

US 2006/0057733 A1 Mar. 16, 2006

(51) Int. Cl.
 *G01N 3/02* (2006.01)

(52) U.S. Cl. ...... 422/70; 73/61.52; 73/61.55; 210/198.2

(58) Field of Classification Search ............... 436/161, 436/163; 422/70; 73/61.52–61.58; 210/198.2
See application file for complete search history.

(56) References Cited

U.S. PATENT DOCUMENTS

| | | | | |
|---|---|---|---|---|
| 4,414,842 | A | * | 11/1983 | Small et al. ............. 73/61.52 |
| 4,455,233 | A | * | 6/1984 | Pohl et al. ............. 210/635 |
| 4,751,004 | A | * | 6/1988 | Stevens et al. ............. 210/659 |
| 4,999,098 | A | | 3/1991 | Pohl et al. |
| 5,248,426 | A | | 9/1993 | Stillian et al. |
| 5,296,115 | A | * | 3/1994 | Rocklin et al. ............. 204/454 |
| 5,352,360 | A | | 10/1994 | Stillian et al. |
| 5,433,838 | A | * | 7/1995 | Dasgupta et al. ............. 204/603 |
| 6,036,921 | A | | 3/2000 | Small et al. |
| 6,225,129 | B1 | | 5/2001 | Liu et al. |
| 6,315,954 | B1 | | 11/2001 | Small et al. |
| 6,316,270 | B1 | | 11/2001 | Small et al. |
| 6,316,271 | B1 | | 11/2001 | Small et al. |
| 6,325,976 | B1 | | 12/2001 | Small et al. |
| 6,562,628 | B1 | * | 5/2003 | Liu et al. ............. 436/161 |
| 6,682,701 | B1 | | 1/2004 | Liu et al. |
| 2004/0048389 | A1 | | 3/2004 | Liu et al. |

FOREIGN PATENT DOCUMENTS

| | | |
|---|---|---|
| EP | 0 075 371 A1 | 3/1983 |
| EP | 0133781 A1 | 3/1985 |
| EP | 0 361 234 A2 | 4/1990 |
| EP | 0 555 962 A2 | 8/1993 |
| JP | 60076665 A | 5/1985 |
| JP | 2002-214212 A | 7/2002 |
| WO | WO 03/059822 A3 | 7/2003 |

OTHER PUBLICATIONS

Boring, C.B., et al., "Compact, field-portable capillary ion chromatograph," *J. Chromatogr. A* 804:45-54 (1998).
Pyo, D., et al., "Development of open tubular capillary columns for ion chromatography," *J. Korean Chem. Soc.* 45(2):143-148 (2001).
Rokushika, S., et al., "Micro column ion chromatography with a hollow fibre suppressor," *J. Chromatogr. A* 260:81-87 (1983).

(Continued)

*Primary Examiner* — Jan Ludlow
(74) *Attorney, Agent, or Firm* — Morgan, Lewis & Bockius LLP; David J. Brezner; Gregory C. Ellis

(57) ABSTRACT

An apparatus for capillary ion chromatography having a suppressor having flow-through ion exchange packing in a housing and capillary tubing formed of a permselective ion exchange membrane, and at least partially disposed in said ion exchange packing. Also, a recycle conduit for aqueous liquid from the detector to the packing. Further, the capillary tubing may have weakly acidic or weakly basic functional groups. Also, a method for using the apparatus.

35 Claims, 12 Drawing Sheets

OTHER PUBLICATIONS

Sjögren, A., et al., "Capillary ion chromatography with on-line high-pressure electrodialytic NaOH eluent production and gradient generation," *Anal. Chem.* 69(7):1385-1391 (Apr. 1997).

Dasgupta, P.K. Approaches to Ionic Chromatography. *Ion Chromatography*, James G. Tarter, Ed. Marcel Dekker, Inc., 191-236 and 338-341 (1987).

Gurskii, V.S., N.V. Voronina, and S.V. Timofeev. Capillary suppressor for use in two-column anion-exchange chromatography, *Industrial Laboratory* 62(5):284-285 (1996).

Godon, L.A., V.S. Gurskii, and S.V. Timofeev. A hydroxide eluent generator for ion-chromatographic determination of anions, *Industrial Laboratory(Diagnostics of Materials )* 63(12):716-717 (1997).

* cited by examiner

CAPILLARY ION CHROMATOGRAPHY

BACKGROUND OF THE INVENTION

Ion chromatography (IC) has become a widely used analytical technique for the determination of anionic and cationic analytes in various sample matrices since it was introduced in 1975. Ion chromatography today is performed in a number of separation and detection modes. Ion chromatography with suppressed conductivity detection is the most widely practiced form of the technique. In suppressed conductivity detection, an eluent suppression device, termed a suppressor, converts the eluent into a weakly conducting form and enhances the conductance of target analytes. The original suppressors were columns packed with ion-exchange resins in appropriate ionic forms. Those packed-bed suppressors had a relatively large dead volume and required off-line chemical regeneration. To overcome this problem, suppressors based on ion-exchange fibers and other membranes were developed. These suppressors can be continuously regenerated using either acid or base regenerant solutions.

One disadvantage associated with the original membrane suppressors was that an external source of either acid or base regenerant solution typically was used to generate the suppressor continuously. Over the years, various designs of electrolytically-regenerated membrane suppressors as described in U.S. Pat. Nos. 4,999,098, 5,248,426, 5,352,360, and 6,325,976 have been developed to overcome the limitations associated with the chemically-regenerated membrane suppressors. The electrolytic suppressors offer several advantages in ion chromatography. They provide continuous and simultaneous suppression of eluents, regeneration of the suppression medium, and sufficient suppression capacity for common IC applications. They are easy to operate because the suppressed eluent or water can be used to create regenerant ions electrolytically. Thus, there is no need to prepare regenerant solutions off-line. Also, the suppressors are compatible with gradient separations. They have very low suppression zone volume, which makes it possible to achieve separations with high chromatographic efficiency.

In ion chromatography, dilute solutions of acids, bases, or salts are commonly used as chromatographic eluents. Traditionally, these eluents are prepared off-line by dilution with reagent-grade chemicals. Off-line preparation of chromatographic eluents can be tedious and prone to operator errors, and often introduces contaminants. For example, dilute NaOH solutions, widely used as eluents in the ion chromatographic separation of anions, are easily contaminated by carbonate. The preparation of carbonate-free NaOH eluents is difficult because carbonate can be introduced as an impurity from the reagents or by adsorption of carbon dioxide from air. The presence of carbonate in NaOH eluents can compromise the performance of an ion chromatographic method, and can cause an undesirable chromatographic baseline drift during the hydroxide gradient and even irreproducible retention times of target analytes. In recent years, several approaches that utilize the electrolysis of water and charge-selective electromigration of ions through ion-exchange media have been investigated by researchers to purify or generate high-purity ion chromatographic eluents. U.S. Pat. Nos. 6,036,921, 6,225,129, 6,316,271, 6,316,270, 6,315,954, and 6,682,701 describe electrolytic devices that can be used to generate high purity acid and base solutions by using water as the carrier. Using these devices, high purity, contaminant-free acid or base solutions are automatically generated on-line for use as eluents in chromatographic separations. These devices simplify gradient separations that can now be performed using electrical current gradients with minimal delay instead of using a conventional mechanical gradient pump.

The combined use of the electrolytic eluent generator and suppressor has significantly changed the routine operation of ion chromatographic methods and permits the performance various ion chromatographic separations using only deionized water as the mobile phase. The use of these electrolytic devices results in significant improvements in the performance of ion chromatography methods by allowing minimal baseline shifts during the gradients, greater retention time reproducibility, lower detection backgrounds, and lower detection limits for target analytes.

Recently, capillary high performance liquid chromatography using separation columns with internal diameters of 1 mm or smaller has gained increasing popularity as an analytical separation tool because of the advantages associated with the miniaturization of separation processes. The typical separation columns in ion chromatography have column internal diameters ranging 2 mm to 4 mm and are operated in flow rate ranging from 0.2 to 3 mL/min. The practice of ion chromatography in the capillary format (i.e., using small bore columns with internal diameters of about 1 mm or smaller) potentially has a number of advantages for analysis of ionic analytes. The use of capillary separation column can improve the separation efficiency and/or speed. Separation processes in the capillary format require much smaller amount of sample and thus offer improved compatibility with applications where amount of sample is limited. Capillary ion chromatography system typically operates at 1 to 20 µL/min and thus the amount of eluent consumed is very small. Capillary ion chromatography has improved capability for continuous operation with minimal intervention and thus minimizes problems associated with system start-up and shutdown. The operation of capillary ion chromatography at low flow rates improves the system compatibility with mass spectrometer. In addition, the practice of ion chromatography in the capillary format opens the door for the possibilities of offering new selectivity for difficult applications using new columns packed with more exotic and difficult-to-make stationary phases.

When compared to high performance liquid chromatography, ion chromatography has progressed slower in the area of miniaturization of the dimension of the separation process. A limited number of studies have been reported so far in the area of capillary ion chromatography using suppressed conductivity detection. In 1983, Rokushika and co-workers reported the development of a capillary ion chromatography system using suppressed conductivity detection (*J. Chromatography*, 260 (1983) 81-88). In their study, an anion exchange capillary column was prepared by packing a surface-agglomerated anion exchange resin in a fused silica capillary with an internal diameter of 190 µm. The suppressor was fabricated using a Nafion® hollow fiber tubing and was regenerated chemically using an external solution of 0.05 M deodecylbenzenesulfonic acid. Separations of inorganic anions and carboxylic acids were disclosed. In 1997, Dasgupta and coworker reported the implementation of a capillary ion chromatography system using an on-line high pressure electrolytic sodium hydroxide eluent generator (*Anal. Chem.*, 29 (1997) 1385-1391). In their system, deionized water was used as the carrier for electrolytic generation of sodium hydroxide eluents at 2 µL/min typically, a capillary column packed with anion exchanger was used as the separation column, and a suppressor prepared using Nafion® tubing and regenerated chemically using a solution of sulfuric acid was used. Both isocratic and gradient separations of inorganic and organic anions were disclosed. In 2001, Pyo and Kim reported their work on the development of capillary ion chromatography using open tubular columns and suppressed conductivity detection (*J. Korean Chem. Soc.,* 2001, Vol. 45, No. 3). Open tubular capillary columns coated with DMEOHA latex particles were used as separation columns. The suppressor was fabricated using a Nafion® hollow fiber tubing and regenerated chemically using an external acid solution.

In the publications discussed above, capillary ion chromatography with suppressed conductivity detection was performed using suppressors made of ion-exchange capillary tubing. These publications disclose chemical regeneration using an external dilution acid solution. The dead volume of this type of suppressors can be minimized so that they are compatible with the capillary separation columns. However, these publications disclosed the use of chemical regenerant, adding costs of dispensing and disposing of the chemical regenerant, resulting in potential leakage of the chemical regenerant across the ion-exchange membrane into the eluent, which raises the conductivity detection background and affects negatively the sensitivity of some analytes. There is a need for a capillary ion chromatography system with an easy-to use, rugged, and reliable capillary suppressor.

SUMMARY OF THE INVENTION

One embodiment of the present invention is an apparatus for capillary ion chromatography comprising a suppressor comprising flow-through ion exchange packing in a housing including a packing inlet and a packing outlet, and capillary tubing having an inlet and an outlet and formed of a permselective ion exchange membrane, said tubing being at least partially disposed in said ion exchange packing.

Another embodiment of the invention is an apparatus for capillary ion chromatography comprising (a) a suppressor comprising capillary tubing having an inlet and an outlet and formed of a permselective ion exchange membrane, said tubing being at least partially disposed in a flow-through housing, (b) a flow-through detector in fluid communication with said capillary tube, and (c) a recycle conduit for directing recycled aqueous sample liquid from said detector through said flow-through housing to the outside of said tubing.

Another embodiment of the invention is a suppressor comprising capillary tubing having an inlet and an outlet and formed of a permselective ion exchange membrane, said tubing being at least partially disposed in a flow-through housing, in which the outer wall of said capillary tubing comprises exchangeable ions comprising weakly acidic or weakly basic functional groups.

A further embodiment of the invention is a method for capillary ion chromatography including the steps of (a) flowing an aqueous sample stream including separated sample ionic species of one charge, positive or negative, in an eluent, through capillary tubing formed of a permselective ion exchange membrane, said tubing being packed in flow-through ion exchange packing, and transporting counterions in said eluent of opposite charge to said sample ionic species across said tubing from the inner wall to the outer wall thereof, and (b) flowing an aqueous regenerant liquid through said ion exchange packing past the outside of said tubing to carry away the transported counterions transported to said outer tubing wall.

A further embodiment of the invention is a method for capillary ion chromatography including the steps of (a) flowing an aqueous sample stream including separated sample ionic species of one charge, positive or negative, in an eluent, through capillary tubing formed of a permselective ion exchange membrane, and transporting counterions in said eluent of opposite charge to said sample ionic species across said tubing from the inner wall to the outer wall thereof, (b) detecting said separated ionic species exiting said capillary tubing by flowing the liquid sample stream through a detector, and (c) recycling said aqueous sample stream from said detector to said outer tubing wall to carry away said counterions transported to the same.

DETAILED DESCRIPTION OF THE PREFERRED EMBODIMENTS

The system of the present invention is useful for determining a large number of ionic species. The species to be determined are solely anions or solely cations. Suitable samples include surface waters, and other liquids such as industrial chemical waste, body fluids, beverages, and drinking water. When the term "ionic species" is used, it includes species in ionic form and components of molecules which are ionized under the conditions of the present invention.

In general, the present invention relates to ion chromatography apparatus and method in which the chromatography is performed on a capillary scale. Ion chromatography systems of the present invention include (a) a capillary separation column, typically in the form of a chromatography column, (b) a suppressor in which the effluent from the chromatography column flows through a capillary-sized tubing in the suppressor ("a capillary suppressor"), and (c) a detector, typically a conductivity detector, downstream of the suppressor The term "capillary tubing" is defined to encompass narrow bore capillary tubing as generally used in chemical analysis but is not limited to such capillary tubing. Instead, the term "capillary tubing" broadly includes tubing having the dimensions on the order of magnitude of the internal dimensions of prior art capillary tubing. Such capillaries typically have a bore diameter ranging from about 5 to 1,000 microns, more preferably from about 10 to 500 microns. Such dimensions typically apply both to the separator column and the suppressor capillary tubing of the present invention. One or more segments of capillary tubes may be joined to form continuous capillary tubing. The capillary tubing leads to capillary flow rates, e.g. 0.1 to 50 µL/min.

In general, any of the well-known ion chromatography systems, e.g., as illustrated in U.S. Pat. Nos. 3,897,213, 3,920, 397, 3,925,019 and 3,956,559 may also be employed but using the capillary suppressors of the present invention.

Figure 1:
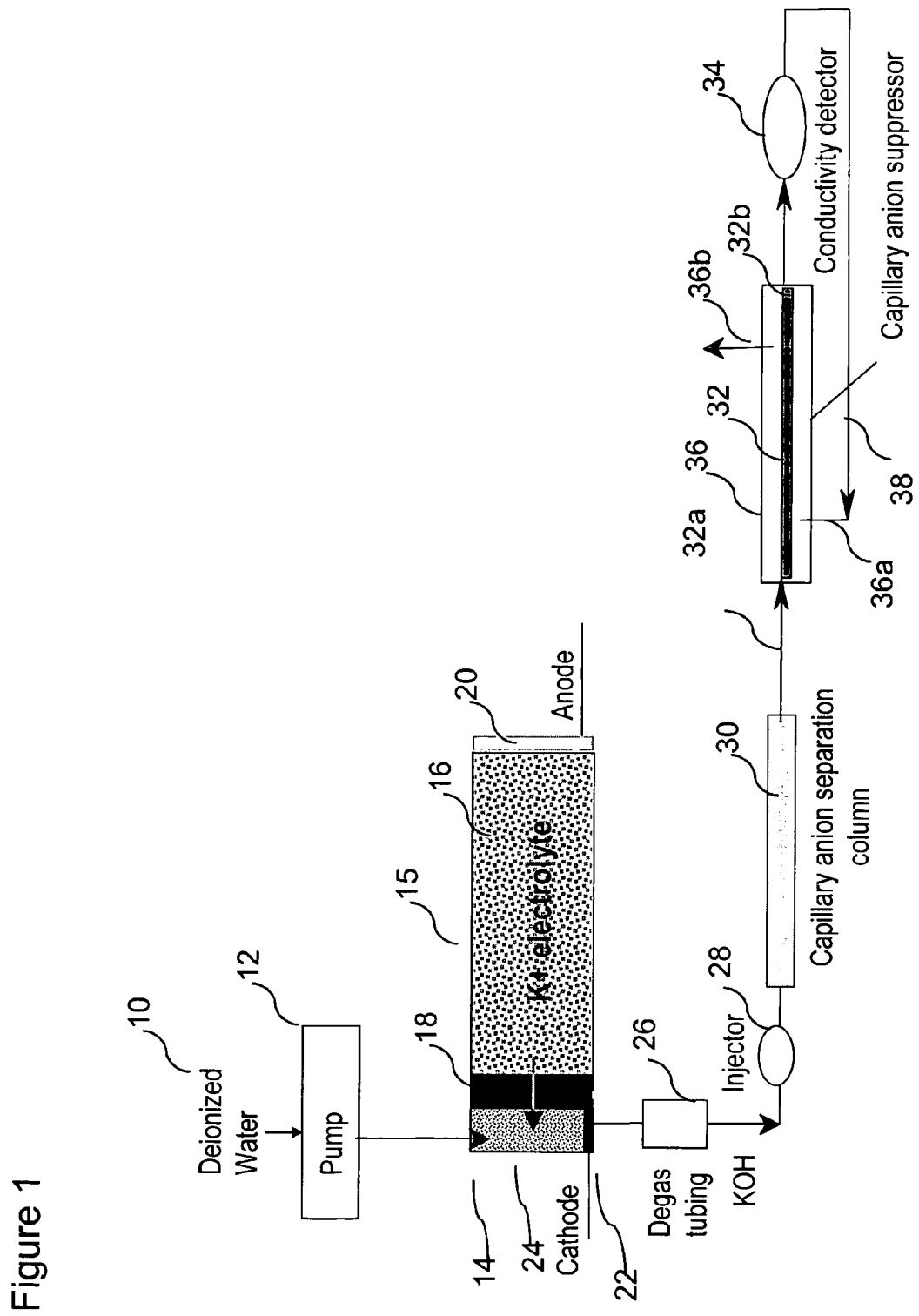
FIGS. 1-5 are schematic representations of different embodiments of the present invention.

In one embodiment of the invention, illustrated in FIG. 1, the capillary suppressor of the present invention is illustrated schematically. In this embodiment, an eluent generator of the type illustrated in FIG. 1 of U.S. Pat. No. 6,682,701 is used, although other eluent generators as illustrated in that patent or elsewhere can be used in combination with the capillary ion chromatography system of the present invention. The principles of operation of the eluent generator are fully illustrated in this patent. Also, the system of FIG. 1 illustrates a recycle of solution from the detector to the outside of the capillary tubing as will be described more fully hereinafter. Such recycle for different forms of suppressors is illustrated in U.S. Pat. No. 5,248,426.

Referring specifically to the embodiment of FIG. 1, deionized water from a source, not shown, is pumped by pump 12 through high pressure base generator chamber 14 of base generator 15. Chamber 14 is separated from a low pressure ion source reservoir 16 including a source of eluent ion. As illustrated, the system is for anion analysis in which the ions to be supplied for the analyte are cations, potassium ion as illustrated, or sodium, lithium or other cations. The ion source reservoir may be in the form of a base or salt solution which can be replenished as illustrated in the '701 patent. A charged permselective membrane barrier or connector 18 substantially prevents bulk liquid flow while providing an ion transport bridge to transport the potassium ions into the base generation chamber 14. Suitable membranes, e.g. ones formed of Nafion®, are illustrated in the '701 patent. An anode 20, e.g. platinum, is in electrical communication with reservoir 16 and a cathode 22, e.g. platinum, is disposed at the outlet of base generation chamber 14. Cation exchange packing such as a resin bed may be disposed in base generation chamber 12 as illustrated in the '701 patent. Electrolysis is performed to provide the reaction illustrated in the '701 patent so that the base, KOH, is generated in base generation chamber 14. Under the applied electric field, the potassium ions migrate across the ion exchange connector or membrane to combine with hydroxide ions to form a KOH eluent. The concentration of KOH solution formed is proportional to the applied current and inversely proportional to the flow rate of the deionized water carrier stream. Hydrogen is generated at the cathode which could interfere with analysis. Thus, it is preferable to use a degassing tubing device 26 typically using a porous membrane to remove generated hydrogen gases, also illustrated in the '701 patent.

Sample is injected in injector 28 and is carried by the eluent from base generator 15 to ion exchange chromatographic separation column 30. For anion analysis, separation is performed using anion separation medium, typically a packed bed of ion exchange resin in column 30, but of a capillary dimension, as set forth above.

As illustrated, the effluent from capillary anion separation column 30 flows to the inlet 32a of capillary tubing 32, then through the tubing and out outlet 32b and through detector 34, suitably a conductivity detector. Tubing 32 is contained within a suppressor housing 36 which can be any shape including tubular or rectangular. The effluent from the detector 34 is recycled in line 38 to an inlet port 36a of housing 36 and flows outside tubing 32 preferably countercurrently to the flow in tubing 32, and exits outlet port 36b.

Capillary tubing 32 is formed of a permselective ion exchange membrane, suitably of the type described in the prior art, such as formed of Nafion®, to block bulk liquid flow but permit transport of the selected ion, cation in the instance of anion analysis. Thus, the wall of the tubing serves the same purposes as a prior art membrane suppressor or a membrane barrier 18 which can also be formed of Nafion®. The details of the suppressor will be described below.

Other eluent generators may be used with an ionized water source, such as a generator for a carbonate salt such as potassium carbonate illustrated in PCT Application WO/2004/024302. In this instance, the ion chromatography system downstream from the eluent generator also is as illustrated in FIG. 1. Other eluent generators can be used, e.g. as illustrated in U.S. Pat. No. 5,045,204 or U.S. Pat. No. 6,562,628.

Although the eluent generators are illustrated for anion analysis and the generation of cations such as potassium ions, for cation analysis, the same system may be used for generating MSA or other anions for an eluent by appropriate reversal of the polarity of the membrane ion exchange resin and electrodes such as illustrated in U.S. Pat. No. 6,682,701.

It is apparent that the system of FIG. 1 including eluent generation as illustrated above is capable of performing the entire ion chromatography separation process including analyte separation, eluent suppression, and analyte detection using one or more flowing streams of deionized water.

Figure 2:
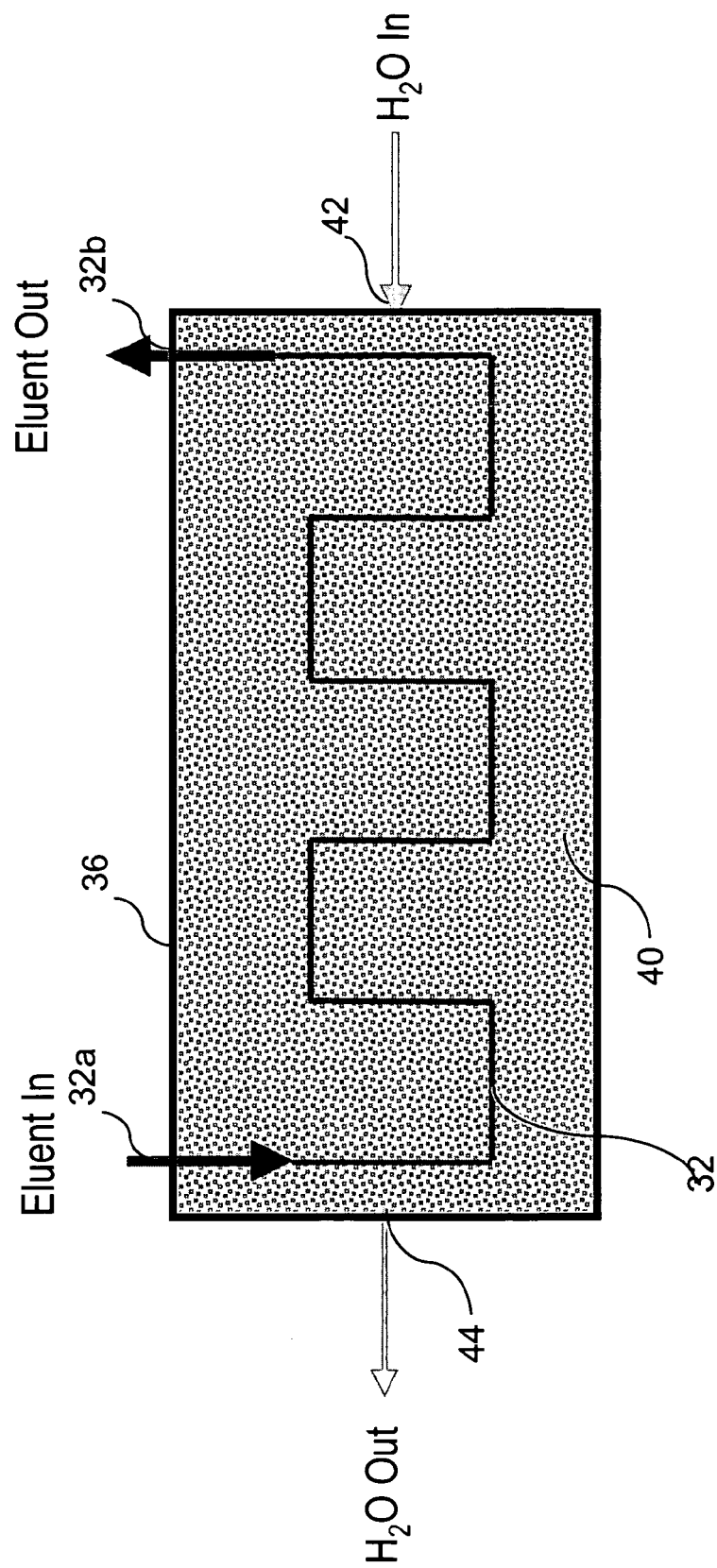

FIG. 2 schematically illustrates an embodiment of a capillary suppressor according to the present invention. Like parts will be designated below with like numbers for FIGS. 1 and 2. As illustrated, suppressor housing 36, suitably formed of a non-conductive, e.g. plastic, column with flow-through ports, include capillary tubing 32 with an inlet 32a and outlet 32b. The tubing typically projects through liquid tight fittings into and out of housing 36 and project in direct or indirect fluid communication with the outlet of separation column 30. Outlet 32b of tubing 32 projects through the housing and is connected to tubing for fluid communication with the inlet of flow-through detector 34.

For anion analysis, a cation exchange capillary tubing is preferably tightly embedded in cation exchange packing 40, suitably a cation exchange resin bed in direct contact therewith. Packing 40 is contained in a housing 36. As illustrated, separate fluid connections are used for the stream flowing through the capillary tubing. A source of flowing aqueous regenerant liquid flows through packing 40 from inlet 42 in a conduit and through outlet 44 through appropriate fittings. The solution then flows through a conduit to detector 34. In the embodiment of FIG. 1, the water source for inlet 42 is the sample stream effluent from the conductivity detector after detection as illustrated in FIG. 1 which flows in recycle conduit 38 illustrated in FIG. 1.

In one embodiment, cation exchange capillary tubing 32 is made of a Nafion® membrane material or some other form of strongly acidic cation exchange membrane. A typical length of the capillary tubing within the suppressor is about 0.1 to 50 cm, preferably 1 to 20 cm. Preferable internal diameters are between about 0.001 inch to 0.010 inch. In one embodiment, the cation exchange resin for ion separation is preferably a strongly acidic cation exchange resin such as sulfonated resin in the hydronium ion ($H^+$) form.

As used herein, the terms "strongly acidic cation" exchange resin or functional groups as those terms are used in the field of chromatography. Thus, for example, Dowex 50W X8 and Amberlite IR 122 are commonly used strongly acidic cation exchange resins. In this type of resin, the functional groups are typically strong acids with pKa less than 1. Typical strongly acidic functional groups include sulfonic groups.

As used herein, the terms "weakly acidic cation" exchange resin or functional groups as those terms are used in the field of chromatography. Thus, for example, Chelex-100 and Bio-Rex 70, and Amberlite IRC-76 resins are commonly used weakly acidic cation exchange resins. In this type of resin, the functional groups are typically weak acids with pKa greater than 1. Typical weakly acidic functional groups include carboxylic acid, chlorocarboxylic acid, and phosphonic acid groups.

Well-known cation exchange packing 40 in the hydronium form may also be used in this embodiment. Although packing 40 is described in a preferred form of ion exchange resin bed, other forms of packing may be used such as a porous continuous structure with sufficient porosity to permit flow of solution through without undue pressure drop and with sufficient ion exchange capacity to form a conducting bridge of cations or anions between the electrodes. One form of structure is a porous matrix or a sponge-like material formed of sulfonated, cross-linked polystyrene with a porosity of about 10 to 15% permitting a flow rate of about 0.1 to 3 ml/min. without excessive pressure drop.

In an embodiment not shown, if the flow rate of the sample liquid stream in recycle conduit 38 is insufficient for its desired effects carrying away the ions which transport across the wall of tubing 32 and/or for cooling the suppressor for an electrolytic application, then an additional source of flowing aqueous liquid, not shown, may be directed through packing 40. In this instance, the additional source of aqueous liquid may comprise a water stream, e.g. deionized water, which is pumped to the suppressor and either combines into a single stream with the water in the recycle conduit or can be directed in a separate conduit through packing 40. As with suppressors which include the recycle in the prior art, it is preferable to flow the aqueous water through the packing external to the tubing countercurrently to flow in the tubing.

When the aqueous effluent from the conductivity detector is recycled and routed through packing 40, the suppressor can be continuously regenerated as long as there is a continuous flow of water to remove KOH generated in the hydrolysis of the weakly acidic resin in the potassium form. Depending on the chemical properties of the functional groups on the resin, the kinetics of the hydrolysis may become a limiting factor determining the suppression capacity of device with respect to the influx of KOH eluent into the suppressor. A second stream of deionized water flowing through the resin bed of the suppressor which may be at a flow rate higher than the flow rate used in the separation process is preferred since it is expected that the suppression capacity may be improved.

For anion analysis, a sulfonated membrane capillary tubing is used, as a base eluent (e.g., KOH) enters the capillary tubing, potassium ions ($K^+$) exchange with hydronium ions ($H^+$) in the wall of the capillary according to the following equations:

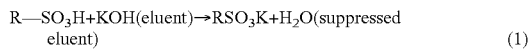
$$R-SO_3H + KOH(\text{eluent}) \rightarrow RSO_3K + H_2O(\text{suppressed eluent}) \quad (1)$$

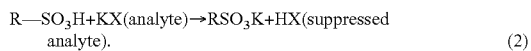
$$R-SO_3H + KX(\text{analyte}) \rightarrow RSO_3K + HX(\text{suppressed analyte}). \quad (2)$$

In the equation, R represents an ion-exchange surface on the capillary. Since the cation exchange capillary is in direct physical contact with the bed of cation exchange resin, $K^+$ ions originally exchanged onto the wall of the cation exchange capillary continue to exchange with $H^+$ ions on the resin beads immediately adjacent to the wall. Subsequently, this exchange process continues to occur among the resin beads that are not in direct physical contact with the cation exchange capillary and located further way from the capillary tubing. In this process, cation exchange resin beads become the source of regenerant ions (i.e., $H^+$ ions) to regenerate the cation exchange capillary tubing. The suppression process continues until the point when the cation exchange beads surrounding the cation exchange capillary become predominant in the potassium form and the incoming flux of hydronium ions to the cation exchange capillary reduce to a level that is insufficient to neutralize the incoming KOH eluent.

The effective suppression capacity of the device at a given eluent concentration and flow rate depends on a number of factors including the length of the capillary, the eluent flow profile inside the capillary, the resin ion exchange capacity, the resin particle size, the amount of the resin surrounding the capillary, the resin bed geometry and the like. The cation exchange capillary tubing can be woven into a geometrical pattern to create torturous flow paths for the eluent going through the capillary to increase the contact of the eluent with the wall of the capillary in order to increase the suppression capacity of the device. The internal opening of the cation exchange capillary may also be filled with an inert or cation exchange monofilament to decrease the dead volume of the capillary suppressor as well as to increase the contact of the eluent with the wall of the capillary in order to increase the suppression capacity of the device. Once the effective suppression capacity of the suppressor is consumed, the resin bed of the device can be regenerated off-line using an external source of acid to convert the entire resin bed back to the hydronium form. The constant water flow may facilitate the potassium/hydronium exchange among the ion exchange sites to increase the effective suppression capacity of the device. In the capillary ion chromatography system shown in FIG. 1, the aqueous effluent from the conductivity detector can be recycled and routed through the resin bed of the capillary suppressor. Alternatively, a separate stream of deionized water may be directed through the resin bed of the suppressor to serve the same function.

As illustrated in FIG. 2, capillary tubing 32 is coiled to flow in a serpentine path. Depending on the desired length of suppressor capillary tubing to accomplish suppression, the tubing may be in a straight line or coiled or in any desired configuration. It would not typically be in the illustrated form with right angle turns because of the resistance to flow.

In another embodiment, the suppressor of FIG. 2 may be employed except that the cation exchange resin packing 40 surround the capillary tubing 32 contains weakly acidic functional groups in addition to strongly acid functional groups. The $H^+$ ions associated with the cation exchange resin particles surrounding capillary 32 act as the source of regenerant ions (i.e., $H^+$ ions) and support the suppression process. $K^+$ ions originally exchanged onto the wall of the capillary continue to exchange with $H^+$ ions on the ionic exchange resin beads immediately adjacent to the wall. This exchange process continues to occur in the resin beads not in direct physical contact with the wall of tubing 32 located further away from the wall. At the same time, the weakly acidic resin in potassium form can undergo the hydrolysis reaction according to the following equation:

$$R-CO_3K + H_2O \rightarrow R-CO_3H + KOH \quad (3)$$

When there is a constant flow of water going through the resin bed, KOH formed in the resin hydrolysis reaction can be routed out of the resin bed. The regenerated resin then becomes available again for the suppression process according to the following equation:

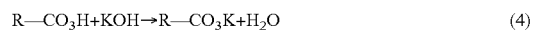
$$R-CO_3H + KOH \rightarrow R-CO_3K + H_2O \quad (4)$$

The effective suppression capacity of the device at a given eluent concentration and flow rate depends on a number of factors including length of the capillary, the eluent flow profile inside the capillary, the resin ion exchange capacity, the resin particle size, the amount of the resin surrounding the capillary, the resin bed geometry, etc. In this embodiment, the resin bed may also consist of a mixture of both strongly acid cation exchange resin and weakly acidic cation exchange resin. This can be done in a uniform or non-uniform mixture of the two different types of resin. In this resin mixture, the weakly acidic cation exchange resin can be regenerated continuously through hydrolysis as described above. This offers the advantage of continuous operation without the need of off-line regeneration with an external acid solution.

Figure 3:
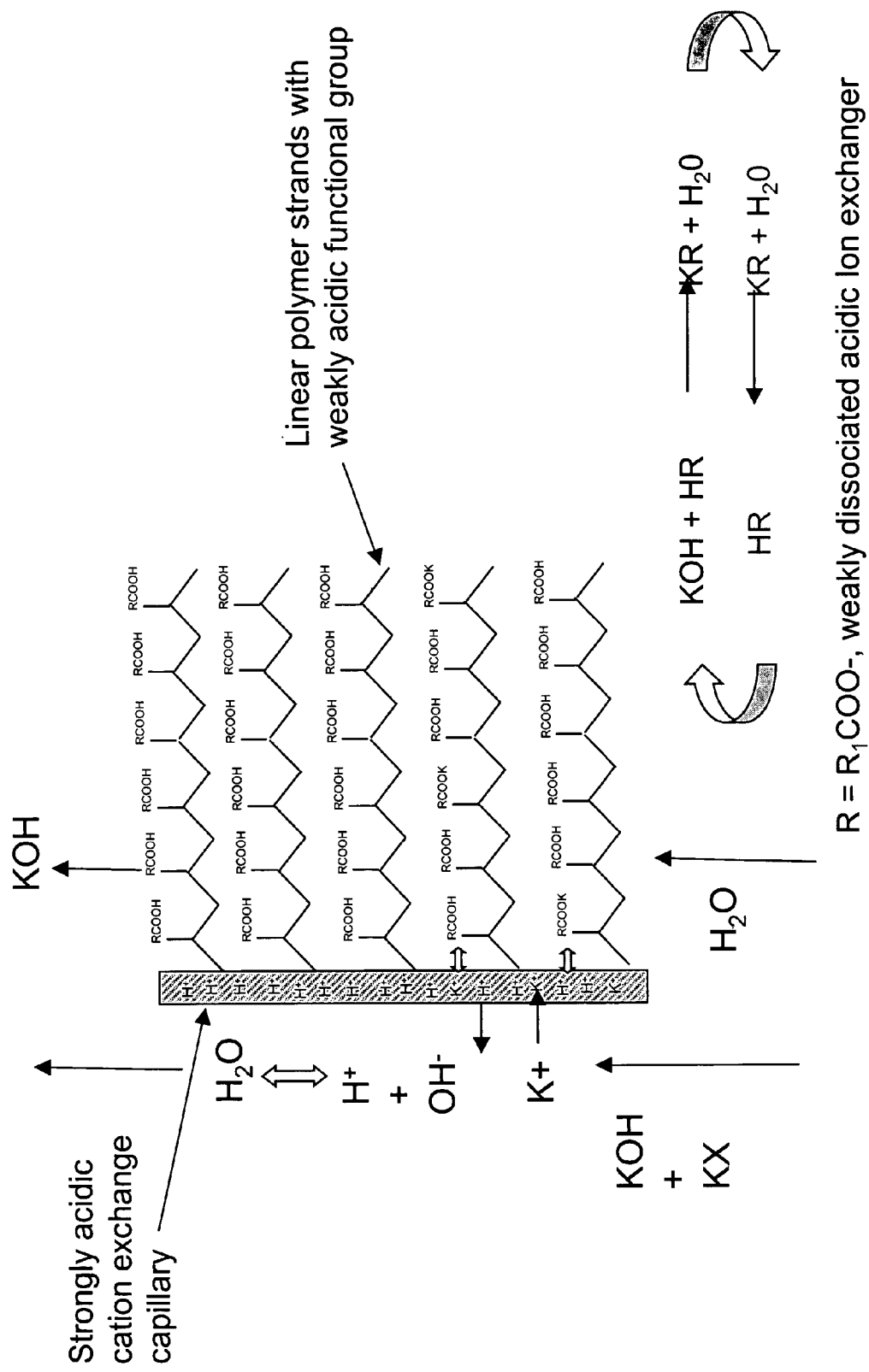

Another embodiment of capillary tubing 32 for use in the suppressor of the present ion invention for anion analysis is depicted in schematic FIG. 3. In this embodiment, the cation exchange capillary contains both strongly acidic and weakly acidic functional groups. FIG. 3 schematically illustrates a cross-section of the cation exchange capillary used in this embodiment. The inner wall of the cation exchange capillary is largely made of ion exchange material containing strongly acidic functional group. The outer wall of the capillary includes weakly acidic functional groups (e.g., bound to the capillary by grafting to the strongly acidic capillary tubing with linear polymers that include such groups. Techniques suitable for the modification of the capillary polymer surface by graft polymerization of a monomer of monomers from active sites generated on solid polymer surfaces are well known (See, e.g., *Encyclopedia of Polymer Science and Engineering*, Supplement Vol, $2^{nd}$ edition, John Wiley & Sons (1989) 678, *Macromolecules*, Vol. 9, (1976), 754, and *Macromolecules*, Vol. 12, (1979), 1222). The most common technique is γ-radiation using radiation sources such as $^{60}$Co source, which generates surface radicals, but thermal, photochemical, plasma, and wet chemical methods can also be used to introduce free radical sites for initiation. Monomers can be present in the gas phase, in solution, or as neat liquids. The surface graft polymerization techniques can be used to modify the ion exchange capillary to include weakly acidic function groups on the outer wall of the capillary.

As the KOH eluent enters into the capillary tubing, potassium ions ($K^+$) exchange with hydronium ions ($H^+$) on the inner wall of the capillary. Subsequently, $K^+$ ions originally exchanged onto the inner wall of the cation exchange capillary continue to exchange with $H^+$ ions on the weakly acidic functional group attached to the outer wall of the capillary. As described previously, the weakly acidic functional groups in potassium form can undergo the hydrolysis reaction according to the following equation:

$$R\text{—}CO_3K + H_2O \rightarrow R\text{—}CO_3H + KOH \qquad (5)$$

KOH formed in the hydrolysis reaction can be routed outside of the plastic housing 36 when there is a constant stream of water flowing outside the cation exchange capillary 32. In this mode of operation, the suppressor can be continuously regenerated as long as there is a continuous flow of water to remove KOH generated. The aqueous effluent from the conductivity detector 34 can be recycled and routed to flow outside of the cation exchange capillary. A second stream of deionized water suitably at flow rates higher than the flow rate used in the separation process may be used since it is expected that the suppression capacity may be improved. In this embodiment, the weakly acidic functional groups attached to the outer wall of the capillary tubing can be regenerated continuously through electrolysis as described above. This offers the advantage of continuous operation without the need for off-line regeneration with an external acid solution.

Figure 4:
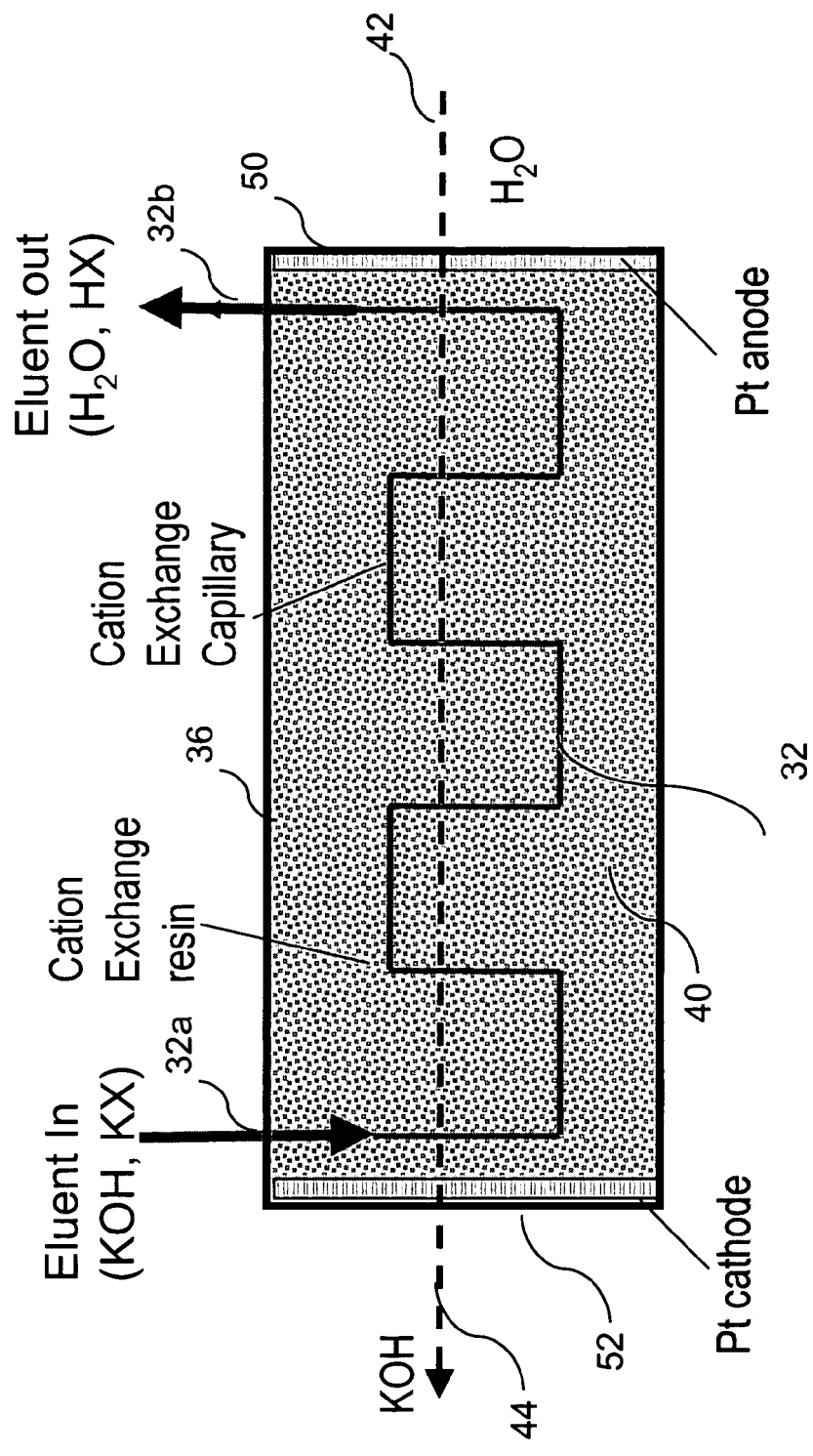

FIG. 4 illustrates an embodiment of an electrolytic capillary suppressor capable of continuous operation for anion analysis. Like parts for FIGS. 2 and 4 are illustrated with like numbers. In this embodiment, as in the embodiment of FIG. 2, the capillary anion suppressor includes a cation exchange capillary tubing 32 embedded tightly inside a bed of cation exchange resin 40 housed in plastic column housing 32 with flow-through ports. The inlet of the resin bed is fitted with a flow-through anode 50, e.g., perforated Pt anode, and the outlet of the resin bed is fitted with a flow-through cathode 52, e.g., a perforated Pt cathode. Both electrodes are preferably in direct contact with packing 40 of the foregoing type. The cation exchange capillary tubing may be made of the foregoing materials in the foregoing dimensions. In the operation of this type of electrolytic capillary suppressor, the resin bed is continuously regenerated by hydronium ions generated through the electrolysis of water at the device anode. The principles and details of one form of continuous electrolytic suppression are illustrated in U.S. Pat. No. 6,468,804. As in FIG. 1, the water used in electrolysis can be supplied the aqueous effluent (i.e., the suppressed eluent) recycled from the conductivity detector. Also, as set forth above, a separate stream of deionized water may be directed through the resin bed in place of or supplemental to the recycle stream.

In another embodiment of the electrolytic capillary suppressor (not shown), the operation of this suppressor is same as the embodiment shown in FIG. 4 except that the water used for electrolytic reactions is routed into the resin bed through a liquid connecting port located near the center of the packing 40, e.g., in the center bottom of FIG. 4. In this configuration, the water is splitting into two streams (one stream flowing out the device anode 50 and the other stream going through the device cathode 52) before exiting the device. One advantage of this embodiment is that the gases (i.e., oxygen at the anode and hydrogen at the cathode) formed during the electrolytic reaction are swept out of the device instead of going through the resin bed, which may lead to improve suppressor performance.

Figure 5:
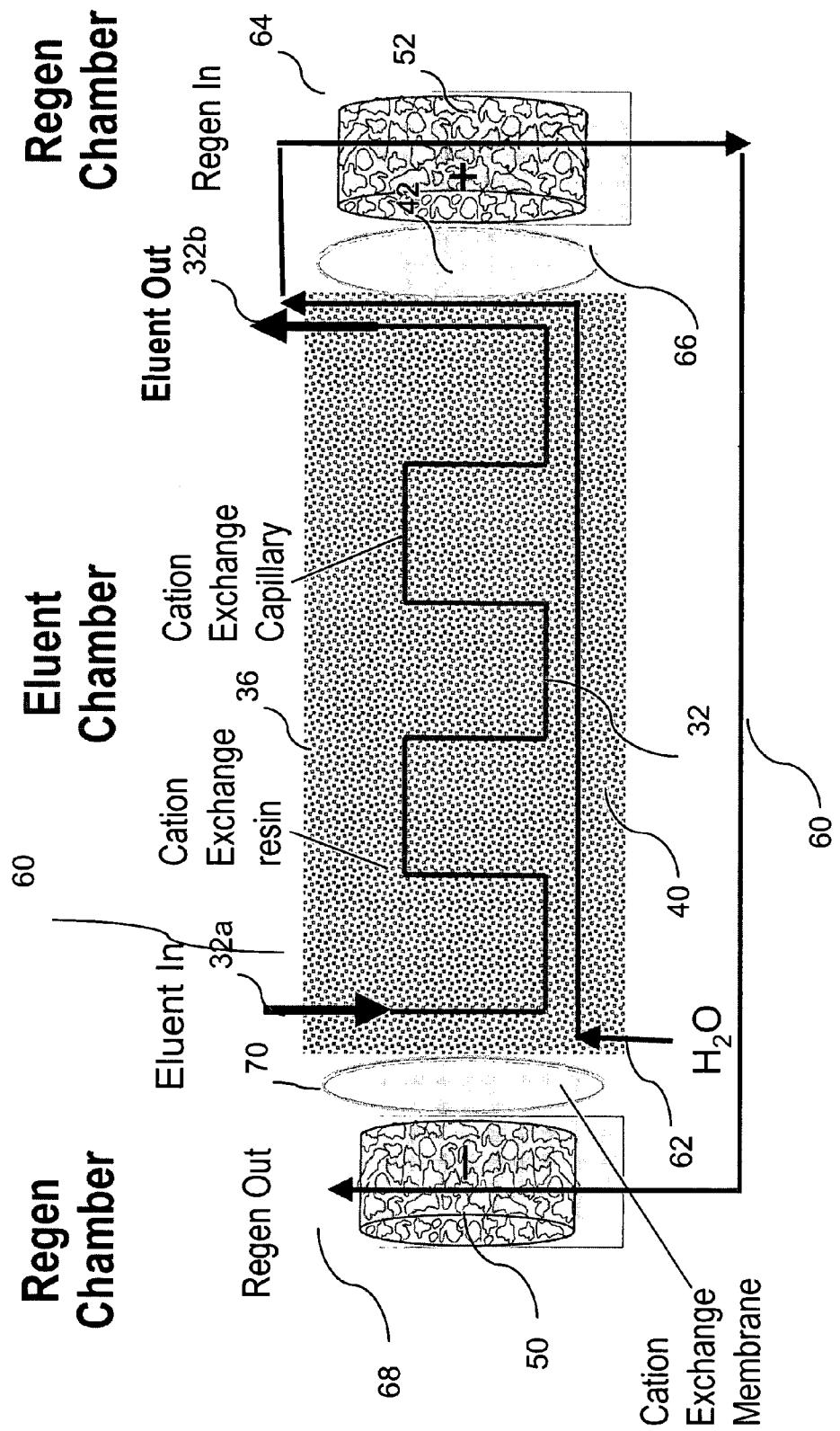

FIG. 5 illustrates another embodiment of the electrolytic capillary suppressor for anion analysis. In this embodiment, suppressor 60 includes three chambers in which the central chamber comprises ion exchange packing 40 in which capillary tubing 32 is embedded as illustrated above. Like parts designated with like numbers for FIGS. 1-4 for this part of the system. As with the device of FIG. 1, the sample-containing eluent from the chromatographic column flows into inlet 32*a* of the capillary tubing, and the liquid that exits capillary tubing 32*b* flows to the detector. The water source 62 may be recycled from a detector and/or some other source of aqueous liquid. The principal difference between the embodiments of FIGS. 4 and 5 is the presence of one or two electrode chambers out of contact with the flow through packing 40. In this instance, the solution exiting packing 40 flows into electrode chamber 64 in which anode 52 is disposed. As illustrated, optional permselective barrier 66 separates packing 40 from electrode chamber 62. The solution exiting electrode chamber 64 may be recycled in conduit 66 through electrode chamber 68 for cathode 60 which may also be separated by optional barrier 70 from packing 40. The use of separate electrode chambers with or without barriers 68 and 70 for suppressing a packed resin bed is illustrated in the embodiment of FIG. 2 of U.S. Pat. No. 6,027,643. The principal difference between these embodiments is the flow of the sample containing eluent through the resin bed is in contact with it in the '643 patent rather than through a capillary tubing within a resin bed as in the present invention. The general principles of electrolytic operation are the same for the embodiments of FIGS. 4 and 5 with the exception of the isolation of the electrodes from a flow-through the resin bed. It is preferable for the aqueous stream to be routed through the packing 40 for being sent to the anode and cathode chamber for use in the electrolytic reaction. Flow of water through packing 40 serves to remove heat generated in the operation of the electrolytic capillary suppressor.

In the above embodiments of electrolytic capillary ion suppression, suppressors can be operated continuously or intermittently. For intermittent operation, once effective suppression capacity is consumed, the resin bed can be generated electrolytically to remove potassium ions to convert the packing back to the hydronium form for the next cycle. The frequency of such intermittent operation would depend on the device dimensions and the eluent influx.

To permit continuous operation without the need for off-line regeneration of packing 40, a total ion exchange capacity of the packing may be selected to correspond to the amount of capacity necessary for a particular eluent stream. For example, for electrolytic operation as in FIG. 4, the total ion exchange capacity of the packing is least 10 times to as high as 10,000 to 100,000 times or more higher than the ion exchange capacity of the capillary tubing.

By appropriate reversal of the polarity of the packing electrodes and membranes, the capillary suppressors of the prior art can be used for suppressing acid eluents for cation analysis.

In order to further illustrate the present invention, the following non-limiting examples are provided.

EXAMPLE 1

Electrolytic Generation of KOH Eluents at Capillary Chromatography Flow Rates

This example demonstrates the electrolytic generation of KOH solution at capillary chromatography flow rates. A modified Dionex P680 pump (Dionex Corporation, Sunnyvale, Calif.) was used to deliver a stream of deionized water at 10 µL/min. Deionized water was first passed through an ATC-HC column and a CTC-1 column to remove ionic contaminants and then routed into a KOH eluent generator for generation of KOH solution. The KOH eluent generator was prepared by modifying a Dionex EGC-KOH cartridge (P/N 058900). A Keithley Model 220 Programmable Current Source (Keithely Instruments, Inc., Cleveland, Ohio) was used to supply the DC current to the anode and cathode of the KOH eluent generator. A Dionex ED50A conductivity detector equipped with a modified flow-through conductivity cell was used to monitor conductance of the KOH solution formed. A Dionex Chromeleon 6.5 computer workstation was used for instrument control, data collection, and processing.

Figure 6:
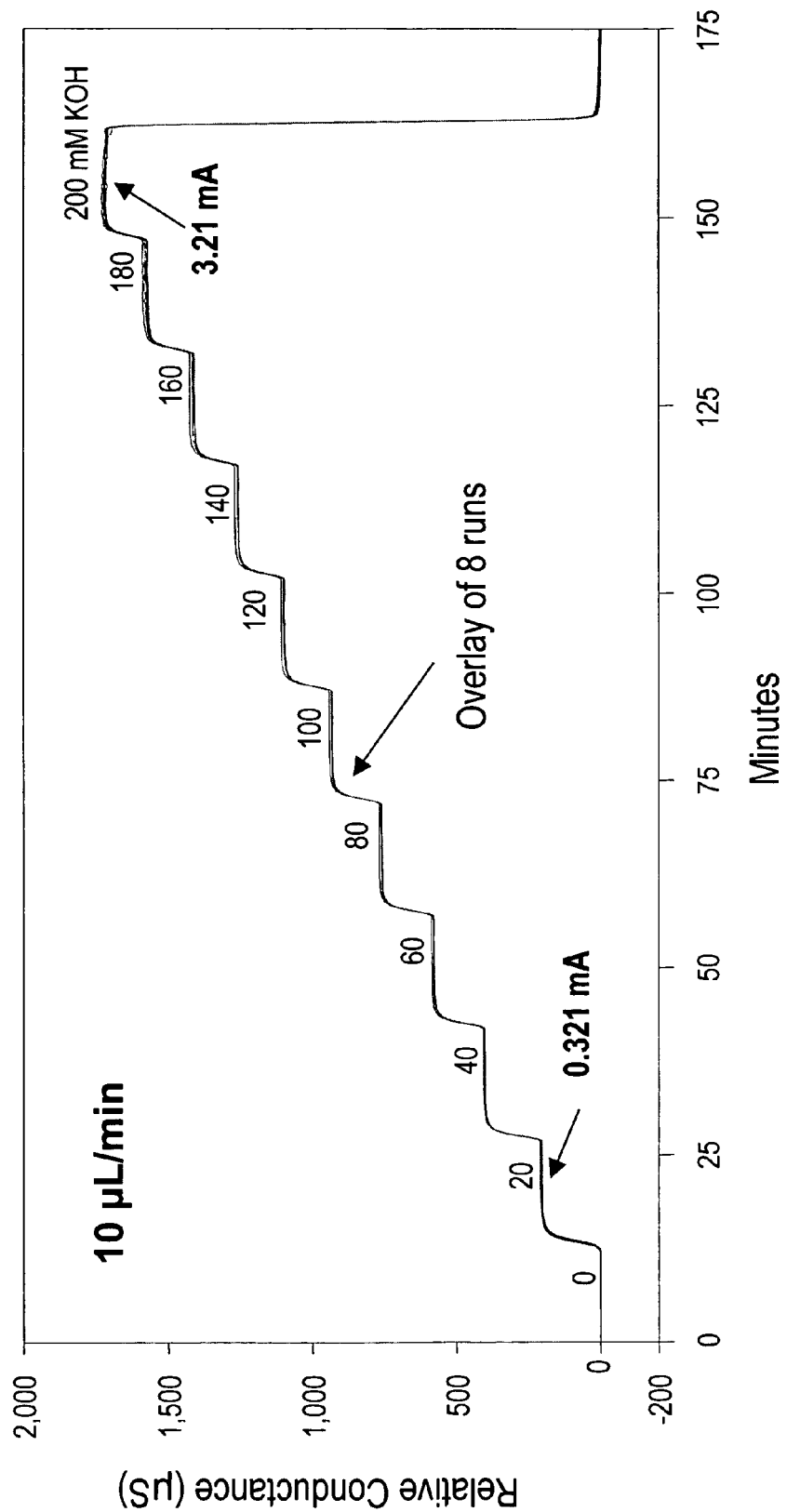
FIGS. 6-12 are charts of different experimental results illustrating the methods and apparatus of the present invention.

FIG. 6 shows an overlay of 8 conductance profiles of KOH eluents generated electrolytically at 10 µL/min. In this example, the DC current applied to the eluent generator was varied from 0 mA to 3.21 mA in 0.321-mA steps to achieve the generation of KOH eluents in concentrations ranging from 0 mM to 200 mM in 20-mM steps. The results shown in FIG. 6 indicate that it is feasible to generate reproducibly KOH solutions over a wide range of concentration at capillary flow rates.

EXAMPLE 2

Use of a Resin-Phase Regenerant Capillary Anion Suppressor in Capillary IC Separation of Common Anions This example demonstrates the use of a resin-phase regenerant capillary anion suppressor of the type depicted in FIG. 2 in capillary IC separation of common anions. The capillary IC system used in the experiment was constructed according to the scheme shown in FIG. 1. A modified Dionex P680 pump (Dionex Corporation, Sunnyvale, Calif.) was used to deliver deionized water at 12 µL/min. To generate a KOH eluent, deionized water was first passed through Dionex ATC-HC and CTC-1 columns to remove ionic contaminants and then routed into a KOH eluent generator that was prepared by modifying a Dionex EGC-KOH cartridge (P/N 058900). A Keithley Model 220 Programmable Current Source (Keithely Instruments, Inc., Cleveland, Ohio) was used to supply the DC current to the anode and cathode of the KOH eluent generator. The outlet of the KOH eluent generator was connected to a high-pressure degas unit to remove hydrogen gas generated during the electrolytic eluent generation process. A Rheodyne six-port PEEK high-pressure injection valve (Cotati, Calif.) was used for injection of samples. The capillary anion separation column was prepared by packing a proprietary Dionex surface-functionalized anion exchange resin in a 1/16-inch OD PEEK tubing of 250 mm in length and 380 µm in internal diameter. A Dionex ED50A conductivity detector equipped with a modified flow-through conductivity cell was used. A Dionex Chromeleon 6.5 computer workstation was used for instrument control, data collection, and processing.

In this example, the capillary suppressor was prepared according the basic scheme illustrated in FIG. 2. A 15-cm length of Nafion® cation exchange capillary tubing (0.004-inch ID×0.010-inch OD) was embedded inside a bed of 8% cross-linked and 20-µm sulfonated styrene divinylbenzene resin beads (Dionex Corporation) that were housed inside a PEEK column (9-mm ID×150 mm in length) with two flow-through liquid connecting ports. Provisions were also made to provide separate fluid connections to the Nafion® cation exchange capillary tubing. The suppressed effluent from the conductivity cell was routed through the resin bed of the suppressor at 12 µL/min.

Figure 7:
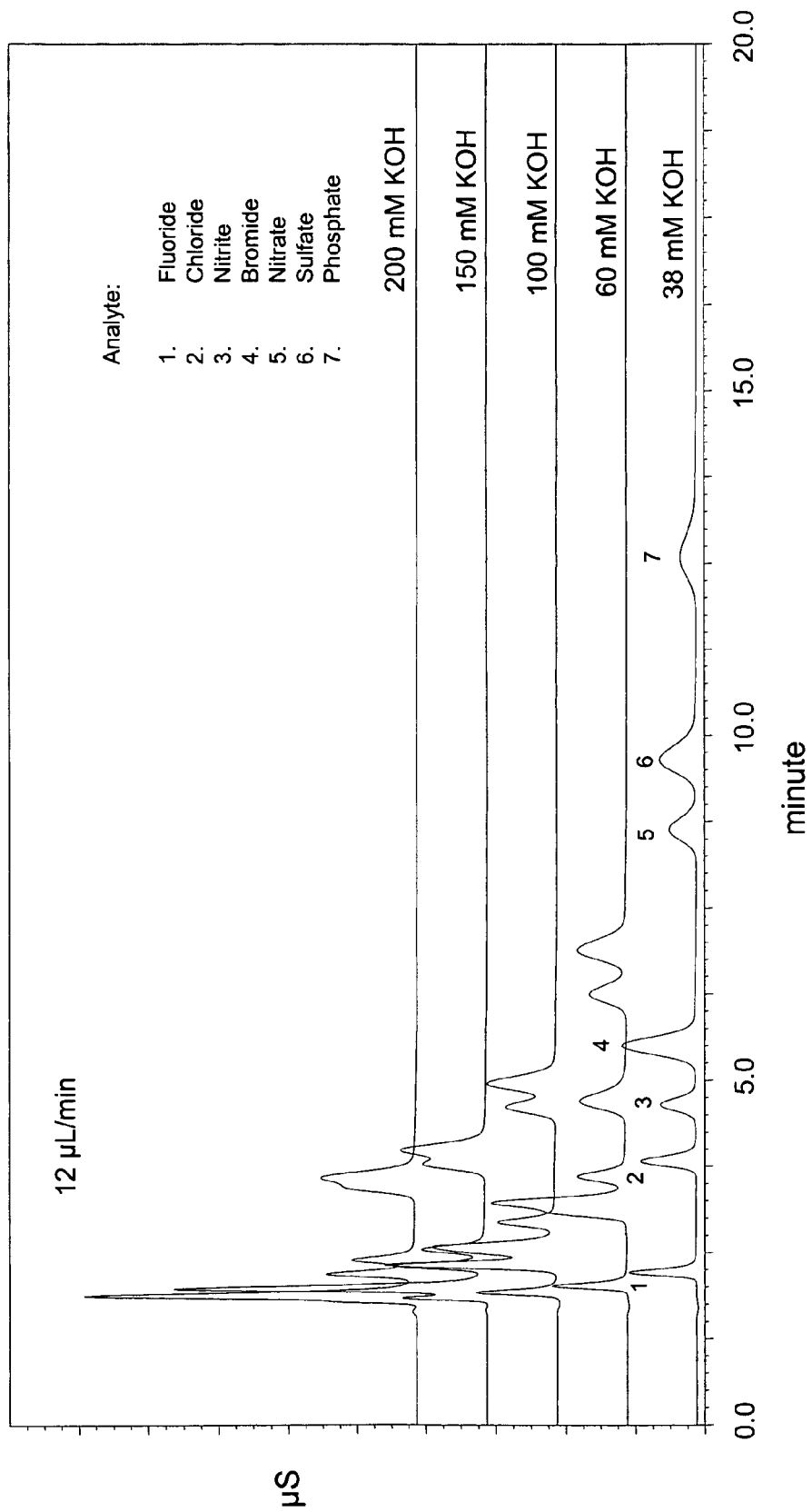

FIG. 7 shows the separation of seven common anions (fluoride, chloride, bromide, nitrite, nitrate, sulfate, and phosphate) obtained using the system described above. The concentration of KOH eluent was varied from 38 mM to 200 mM. Complete resolution of all seven anions was obtained when the concentration of KOH eluent was 38 mM. Co-elution of anions was observed at higher KOH concentrations as expected. The results shown in FIG. 7 indicate that the resin-phase regenerant capillary anion suppressor of the type depicted in FIG. 2 can be used successfully to suppress KOH eluents of different concentrations in capillary IC separation of common anions. More significantly, the results shown in FIG. 7 demonstrate that the capillary IC system depicted in FIG. 1 can be used to perform separation of anions using one flowing stream of deionized water.

EXAMPLE 3

Operation of a Resin-Phase Regenerant Capillary Suppressor in the Suppression of KOH Eluent for Anion Analysis This example demonstrates the use of a resin-phase regenerant capillary anion suppressor of the type depicted in FIG. 2 in capillary IC separation of common anions. The capillary ion chromatography system used in this example was same as that used in Example 2, except that a different resin-phase regenerant capillary anion suppressor was used. In this example, the capillary suppressor was prepared according the basic scheme illustrated in FIG. 2. A 15-cm length of Nafion® cation exchange capillary tubing (0.004-inch ID×0.010-inch OD) was embedded inside a resin bed housed inside a PEEK column (9-mm ID×150 mm in length) with two flow-through liquid connecting ports. Provisions were also made to provide separate fluid connections to the Nafion® cation exchange capillary tubing. The suppressor resin bed was made of a resin mixture of 95% (w/w) of a 8% cross-linked and 20-µm sulfonated styrene divinylbenzene resin (Dionex Corporation) and 5% (w/w) of 200-400 mesh Chelex-100 resin (Bio-Rad Laboratories, Hercules, Calif.). The Chelex-100 resin is a cation exchanger with weakly acidic iminodiacetate functional groups. The suppressed effluent from the conductivity cell was routed through the resin bed of the suppressor at 12 µL/min.

Figure 8:
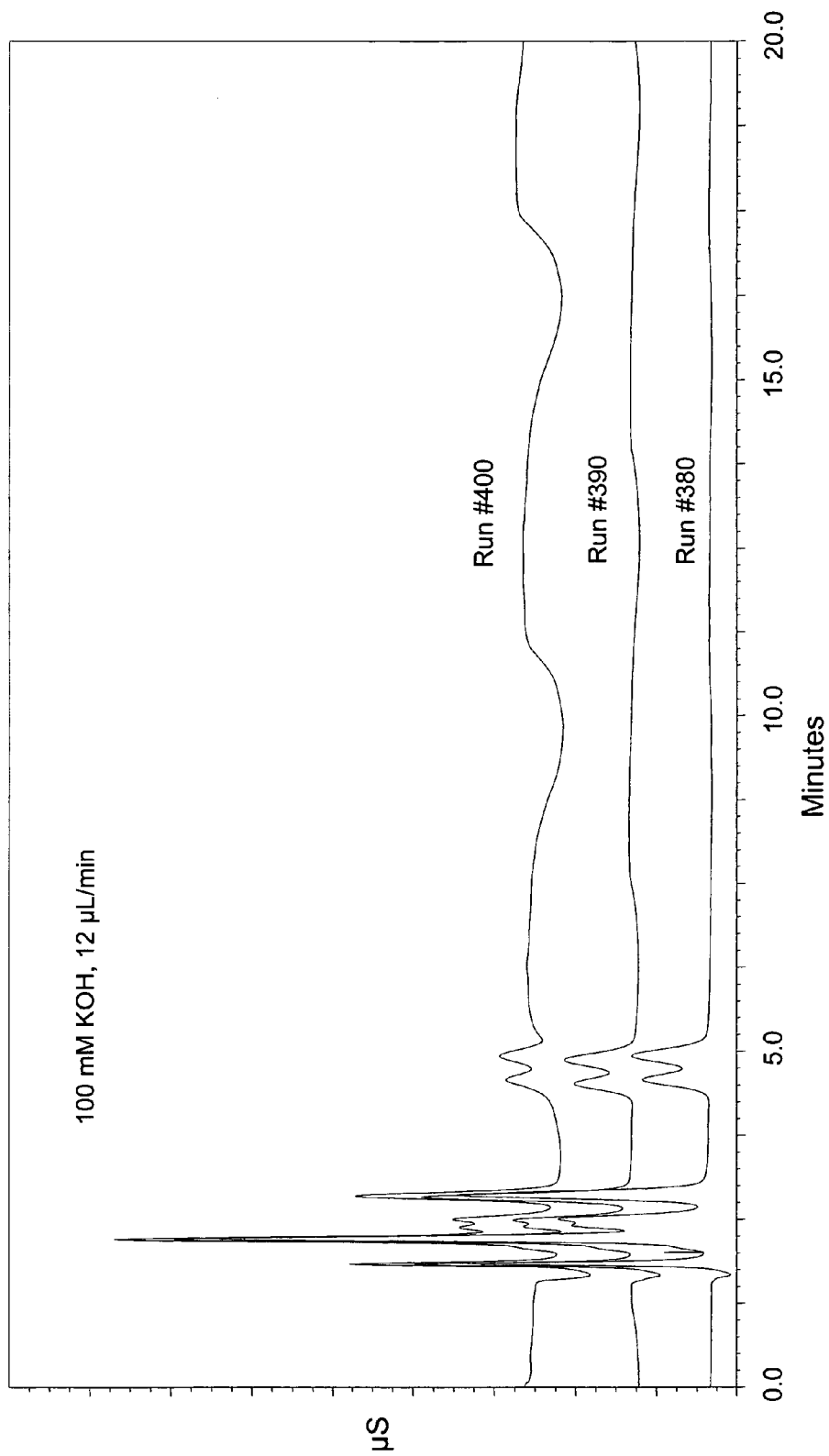

In this example, the separation of seven anions (fluoride, chloride, bromide, nitrite, nitrate, sulfate, and phosphate) on the same capillary anion separation column described in Example 2 was performed continuously for more than 400 runs (each run=20 min) to monitor the longer-term performance of the capillary suppressor. 100 mM KOH was used as the eluent. As shown in FIG. 8, the suppressor provided stable suppressed background for at least 380 runs. A slightly unstable suppressed background was observed for Run #390. A noticeably unstable suppressed background was observed for Run #400. The results shown in FIG. 8 suggest that the resin-phase regenerant capillary anion suppressor of the type depicted in FIG. 2 can functions satisfactorily for an extended period of time in capillary IC separation of common anions. In addition, the results shown in FIG. 8 demonstrate again that the capillary IC system depicted in FIG. 1 can be used to perform separation of anions using one flowing stream of deionized water.

EXAMPLE 4

The Exchange of Cations Among Sulfonated Resin Beads in the Hydronium Form and Sulfonated Resin Beads in the Potassium Form This example illustrates visually the exchange of cations among sulfonated resin beads in hydronium form and sulfonated resin beads in potassium form. In this example, a capillary suppressor was prepared according the basic scheme illustrated in FIG. 2. A 15-cm length of a proprietary grafted and sulfonated TFE capillary tubing of 0.004-inch ID×0.010-inch OD (Dionex Corporation) was embedded inside a bed of 200-400 mesh AG 50W X16 resin, a sulfonated cation exchanger available from Bio-Rad Laboratories (Hercules, Calif.). The resin bed was housed inside a clear glass column (6-mm ID×250 mm in length) available from Bio-Chem Valve, Inc. (Boonton, N.J., USA). Prior to its placement into the glass column, the 200-400 mesh AG 50W X16 resin was homogenously coated with a small amount of quinaldine red, a cationic dye. The coated resin has a golden color when it is in the hydrogen form. The color of the coated resin changes to magenta when it is in the potassium form. Therefore, the color change of the resin can be used to visualize the exchange of cations among sulfonated resin beads in the hydronium form and sulfonated resin beads in the potassium form. The operation of this capillary suppressor was evaluated using the system described in Example 2. The suppressor was used continuously to suppress 20 mM KOH at 10 µL/min. In this example, the suppressed eluent from the conductivity cell was routed to waste. A second stream of deionized water was pumped through the resin bed at 0.25 mL/min.

A slight color change was observed for the resin surrounding the inlet end of the sulfonated TFE capillary in the suppressor after 6 hours of operation. A much noticeable change of resin color was observed for the resin bed at the inlet end of the suppressor after 72 hours of operation. A distinct band of resin in the magenta color was observed for the resin bed at the inlet end of the suppressor after 144 hours of operation. These results demonstrate visually that $K^+$ ions originally exchanged onto the wall of the cation exchange capillary continue to exchange with $H^+$ ions on the resin beads immediately adjacent to the wall, and this exchange process subsequently continues to occur among the resin beads that are not in direct physical contact with the cation exchange capillary and located further way from the capillary tubing.

In another experiment, one drop of quinaldine red coated AG 50W X 16 resin in the potassium form (magenta color) was placed on the bed of quinaldine red coated AG 50W X 16 resin in the hydronium form (golden color) in a beaker. After 2 hours, a noticeable decrease in the intensity of the magenta color was observed. After about 72 hours, the magenta color of the added drop of resin further faded away. After 192 hours, the added drop of resin are hardly distinguishable from the rest of the resin bed, indicating that the added drop of resin was converted to the hydronium form.

EXAMPLE 5

Capillary IC Separation of Anionic Analytes Using Electrolytically-Generated KOH Eluents and Suppressed Conductivity Detection with Electrolytic Capillary Suppressors of the Type Depicted in FIG. 5

This example demonstrates the use of electrolytic capillary anion suppressors of the type depicted in FIG. 5 in the capillary IC separation of common anions. The capillary ion chromatography system used in this example was similar to the one used in Example 2, except that electrolytic capillary anion suppressors were used. In this example, electrolytic capillary suppressors were prepared. The capillary anion suppressors consisted of three PEEK chambers. The eluent chamber contained a cation exchange capillary tubing embedded tightly inside a bed of cation exchange resin (6 to 8 mm ID×10 to 25 mm in length). Provisions were made provide separate fluid connections to the cation exchange capillary tubing in the resin bed. Either a 15-cm length of a proprietary grafted and sulfonated TFE capillary tubing of 0.004-inch ID×0.010-inch OD (Dionex Corporation) or a 15-cm length of Nafion® cation exchange capillary tubing (0.004-inch ID×0.010-inch OD) was used in the construction of electrolytic capillary suppressors. The eluent chamber was physically separated from the cathodic regenerant chamber and anodic regenerant chamber using a proprietary grafted and sulfonated TFE cation exchange ion exchange membranes (Dionex Corporation). The cathode chamber contained a perforated Pt cathode and the anode chamber contains a perforated Pt anode. Both electrode chambers had two liquid connecting ports (inlet and outlet). In this example, the suppressed eluent from the conductivity cell was routed to waste. A second stream of deionized water was first pumped through the resin bed in the eluent chamber, then to the anodic regenerant chamber and the cathodic regenerant chamber at flow rates ranging from 0.1 to 0.25 mL/min. The Dionex ED50A module was used to supply a DC current of 20 mA to the electrolytic capillary suppressors. A Dionex EG40 eluent generator control module was used to supply DC currents to the KOH eluent generation cartridge for generation of KOH eluents used in the ion chromatographic separations of anions.

Figure 9:
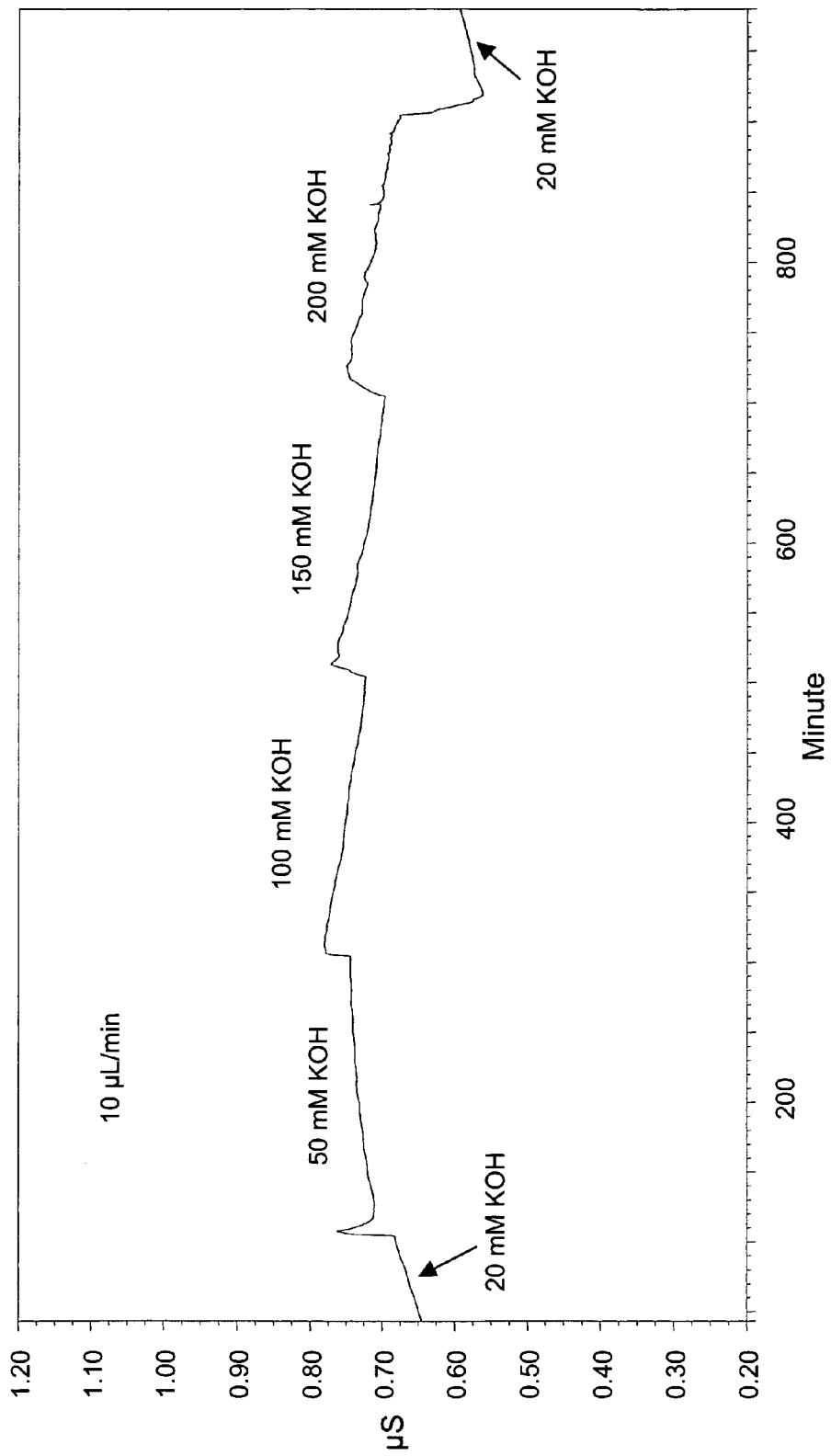

FIG. 9 shows the suppressed conductivity background obtained using the system when the concentration of KOH eluent was varied from 20 to 200 mM at 10 µL/min. The results indicate that the electrolytic capillary suppressor was capable of suppressing KOH at various concentrations effectively.

Figure 10:
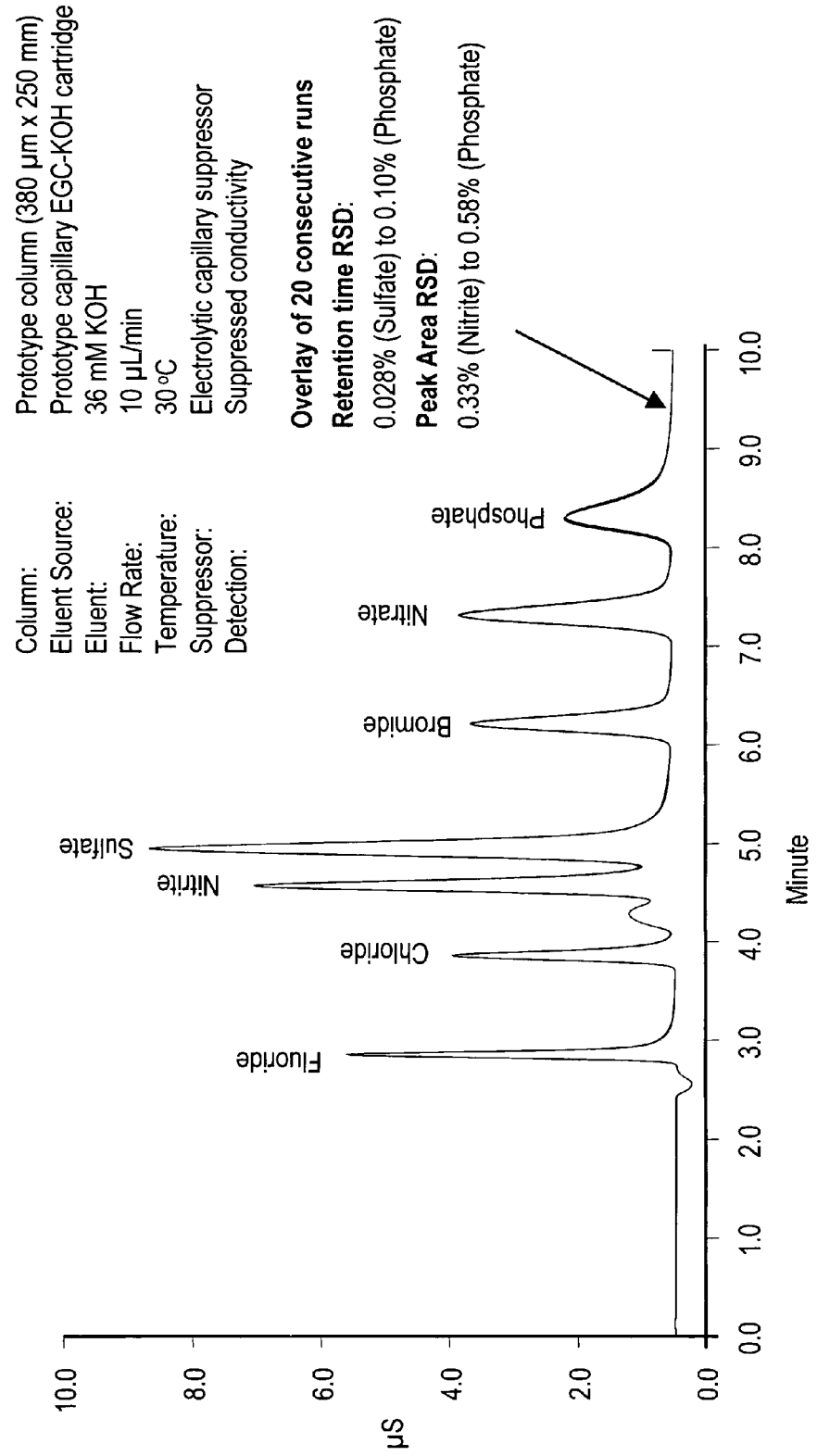

FIG. 10 shows an overlay of 20 consecutive separations of seven common anions (fluoride, chloride, bromide, nitrite, nitrate, sulfate, and phosphate) on a capillary column packed with a proprietary latex-agglomerated anion exchanger (Dionex Corporation). The separation was performed using 38 mM KOH at 10 µL/min. The results show highly reproducible separation of the target anions with analyte retention percent relative standard deviation (RDS) ranging from 0.028% for sulfate to 0.10% for phosphate, and analyte peak area percent RSD ranging from 0.033% for nitrite to 0.58% for phosphate.

Figure 11:
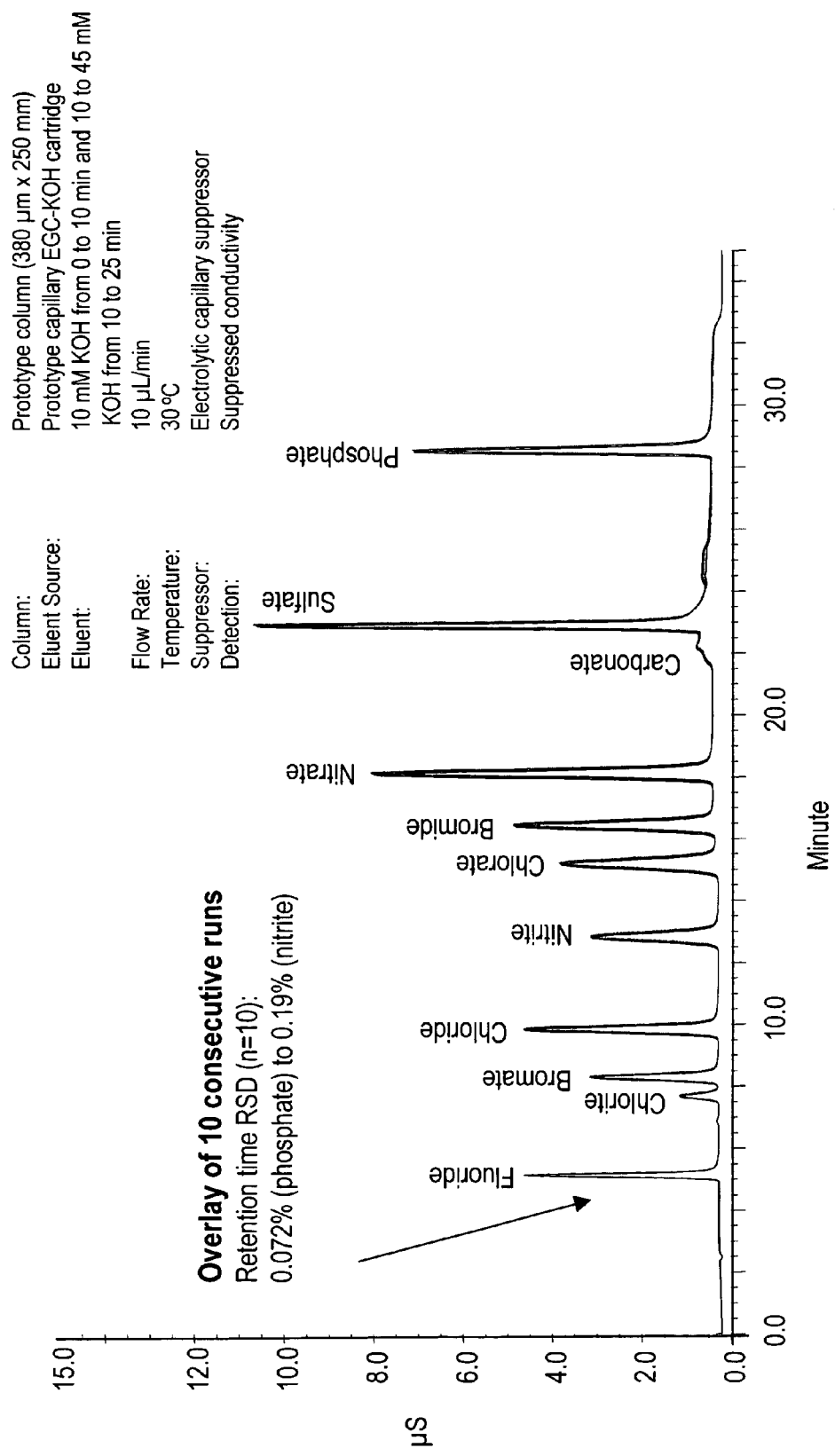

FIG. 11 shows an overlay of 10 consecutive separations of 11 common anions (fluoride, chlorite, bromate, chloride, nitrite, chlorate, bromide, nitrate, carbonate, sulfate, and phosphate) on a capillary column packed with a proprietary surface-functionalized anion exchanger (Dionex Corporation). The separation was performed using KOH eluent with a concentration gradient from 10 to 45 mM KOH at 10 μL/min. The results also show highly reproducible separation of the target anions with analyte retention percent relative standard deviation (RDS) ranging from 0.072% for phosphate to 0.19% for nitrite.

The above results demonstrate that the capillary IC system described in this invention can be used to provide reliable determination of target anionic analytes using only deionized water as the carrier streams.

EXAMPLE 6

Capillary IC Separation of Cationic Analytes Using Electrolytically-Generated MSA Eluents and Suppressed Conductivity Detection with an Electrolytic Capillary Suppressor of the Type Depicted in FIG. 5

This example demonstrates the use of an electrolytic capillary cation suppressor of the type depicted in FIG. 5 in the capillary IC separation of common cations. The basic system components of the capillary ion chromatography system used in this example were similar those depicted in FIG. 1 for cation analysis. The methanesulfonic acid (MSA) eluent generator was prepared by modifying a Dionex EGC-MSA cartridge (P/N 058902). A Keithley Model 220 Programmable Current Source (Keithely Instruments, Inc., Cleveland, Ohio) was used to supply the DC currents to the MSA eluent generation cartridge for generation of MSA eluents used in the ion chromatographic separations of cations.

The electrolytic capillary suppressor was prepared according the basic scheme illustrated in FIG. 5. The capillary anion suppressors consisted of three PEEK chambers. The eluent chamber contained a 15-cm length of a proprietary grafted and aminated TFE capillary tubing of 0.004-inch ID×0.010-inch OD (Dionex Corporation) embedded tightly inside a strongly basic anion exchange resin bed (6 mm ID×20 mm in length). Provisions were made provide separate fluid connections to the cation exchange capillary tubing in the resin bed. The eluent chamber was physically separated from the cathodic regenerant chamber and anodic regenerant chamber using a proprietary grafted and aminated TFE cation exchange ion exchange membranes (Dionex Corporation). The cathode chamber contained a perforated Pt cathode and the anode chamber contains a perforated Pt anode. Both electrode chambers had two liquid connecting ports (inlet and outlet). In this example, the suppressed eluent from the conductivity cell was routed to waste. A second stream of deionized water was first pumped through the resin bed in the eluent chamber, then to the cathodic regenerant chamber and the anodic regenerant chamber at flow rates ranging from 0.2 mL/min. The Dionex SC20 suppressor control module was used to supply a DC current of 15 to 20 mA to the electrolytic capillary suppressor.

Figure 12:
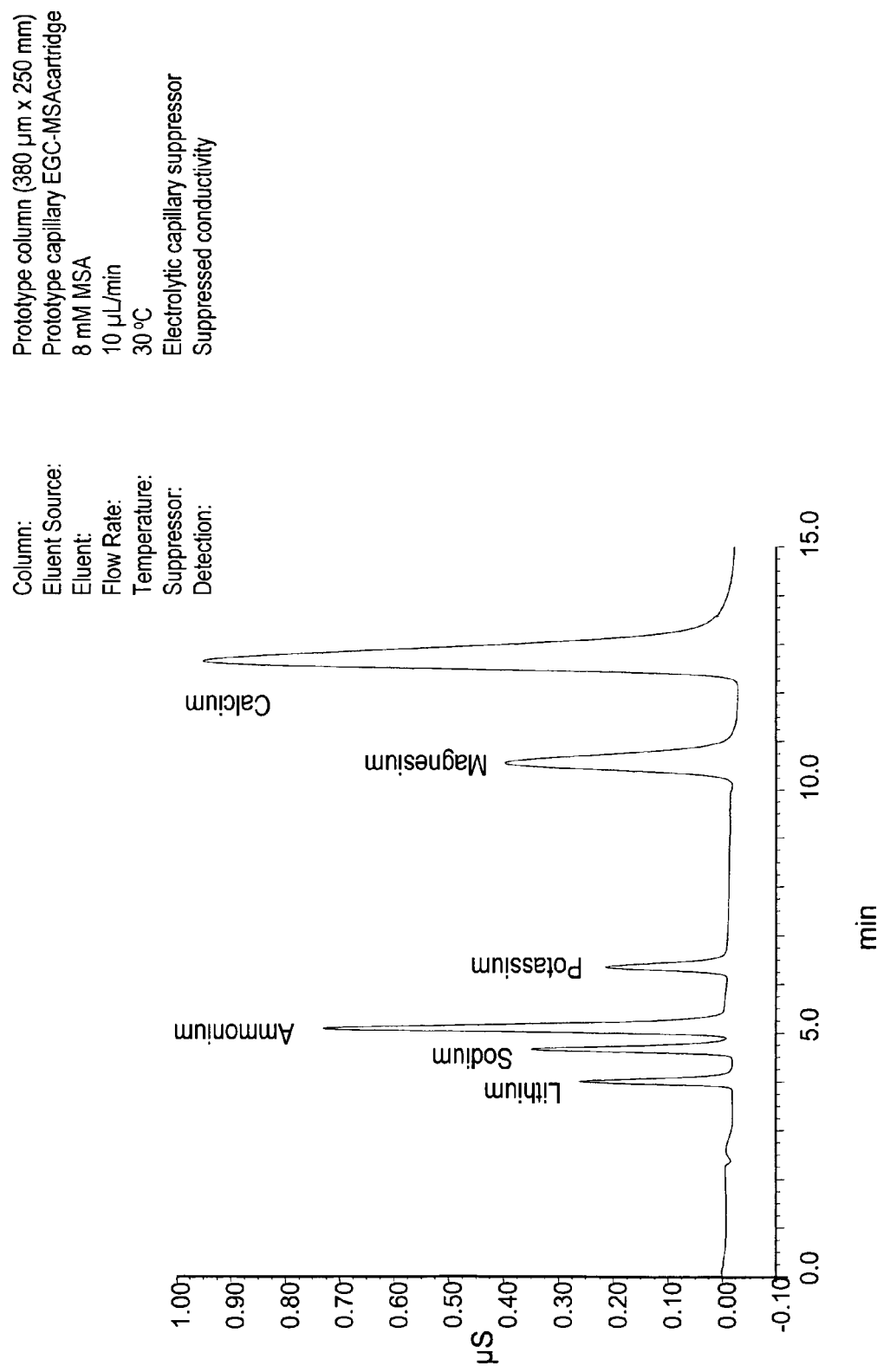

FIG. 12 shows a separation of six common cations (lithium, sodium, ammonium, potassium, magnesium, and calcium) on a capillary column packed with a proprietary surface-functionalized cation exchanger (Dionex Corporation). The separation was performed using 8 mM MSA at 10 μL/min. An excellent resolution of all cationic analytes was obtained. The results demonstrate that the capillary IC system described in this invention can be used to provide separation of target cationic analytes using only deionized water as the carrier streams.

What is claimed is:

1. Apparatus for capillary ion chromatography comprising:
   (a) an electrolytically-regenerated suppressor comprising flow-through ion exchange packing in a housing including a packing inlet and a packing outlet, and capillary tubing having an inlet and an outlet and formed of a permselective ion exchange membrane, said tubing being at least partially disposed in said ion exchange packing, and
   (b) spaced first and second flow through electrodes on opposed sides of said ion exchange packing, wherein said packing inlet is fitted with said first flow through electrode and said packing outlet is fitted with said second flow through electrode.

2. The apparatus of claim 1 further comprising:
   (c) a source of flowing aqueous regenerant liquid in fluid communication with said packing inlet.

3. The apparatus of claim 2 further comprising:
   (d) a capillary chromatography column in fluid communication with said capillary tubing inlet.

4. The apparatus of claim 3 further comprising:
   (e) a flow-through detector in fluid communication with said capillary tubing outlet, and
   (f) a recycle conduit for directing recycled aqueous liquid from said detector to said ion exchange packing, whereby said aqueous regenerant liquid source comprises said recycled aqueous liquid.

5. The apparatus of claim 4 in which said liquid recycled between said detector and flow-through housing is deionized water.

6. The apparatus of claim 4 in which said aqueous liquid source further comprises an additional source of flowing aqueous liquid in addition to said recycled aqueous liquid.

7. The apparatus of claim 1 in which said ion exchange packing includes substrates with exchangeable ions comprising weakly acidic or weakly basic functional groups.

8. The apparatus of claim 1 in which an outer wall of said capillary tubing comprises exchangeable ions comprising weakly acidic or weakly basic functional groups.

9. The apparatus of claim 8 in which an inner wall of said capillary tubing comprises exchangeable ions comprising strongly acidic or strongly basic functional groups.

10. The apparatus of claim 8 in which said weakly acidic or weakly basic functional groups comprise moieties on polymers grafted to the outer wall of said tubing.

11. The apparatus of claim 1 in which said first electrode is disposed in an electrode chamber, said electrode chamber out of contact with said flow through packing.

12. The apparatus of claim 11 in which said second electrode is disposed in an electrode chamber out of contact with said flow through packing.

13. The apparatus of claim 1 in which said housing is formed of a non-conductive material.

14. The apparatus of claim 1 in which said packing is selected to have an ion exchange capacity from at least about 10 to 100,000 times more than the ion exchange capacity of said capillary tubing.

15. Apparatus for capillary ion chromatography comprising:
   (a) an electrolytically-regenerated suppressor according to claim 1,
   (b) a flow-through detector in fluid communication with said capillary tubing, and
   (c) a recycle conduit for directing recycled aqueous sample liquid from said detector through said flow-through housing to the outside of said tubing.

16. The apparatus of claim 15 further comprising flow-through ion exchange packing in said flow-through housing, said tubing being at least partially disposed in said packing, an additional source of aqueous liquid flowing through said packing in addition to said aqueous sample liquid from the detector.

17. The apparatus of claim 15 in which an outer wall of said capillary tubing comprises exchangeable ions comprising weakly acidic or weakly basic functional groups.

18. The apparatus of claim 15 further comprising:
   (a) a capillary chromatography column in fluid communication with said capillary tubing inlet.

19. Apparatus for capillary ion chromatography comprising:
   (a) an electrolytically-regenerated suppressor according to claim 1 wherein an outer wall of said capillary tubing comprises exchangeable ions comprises weakly acidic or weakly basic functional groups.

20. The apparatus of claim 19 further comprising:
   (b) a capillary chromatography column in fluid communication with said capillary tubing inlet.

21. The apparatus of claim 19 further comprising:
   (d) a recycle conduit for directing recycled aqueous liquid from said detector to said ion exchange packing.

22. The apparatus of claim 19 wherein said ion exchange packing includes substrates with exchangeable ion comprising weakly acidic or weakly basic functional groups.

23. The apparatus of claim 19 in which an inner wall of said capillary tubing comprises exchangeable ions comprising strongly acidic or strongly basic functional groups.

24. Apparatus for capillary ion chromatography comprising:
   (a) an electrolytically-regenerated suppressor comprising flow-through ion exchange packing in a housing including a packing inlet and a packing outlet, and capillary tubing having an inlet and an outlet and formed of a permselective ion exchange membrane, said tubing being at least partially disposed in said ion exchange packing,
   (b) spaced first and second flow through electrodes on opposed sides of said ion exchange packing, wherein said packing inlet is fitted with said first flow through electrode and said packing outlet is fitted with said second flow through electrode, and
   (c) a source of deionized water in fluid communication with said packing.

25. Apparatus for capillary ion chromatography comprising:
   (a) an electrolytically-regenerated suppressor comprising flow-through ion exchange packing in a housing including a packing inlet and a packing outlet, and capillary tubing of a diameter from about 5 to 1,000 microns formed of a permselective ion exchange membrane and having an inlet and an outlet, said tubing being at least partially disposed in said ion exchange packing, and
   (b) spaced first and second flow through electrodes on opposed sides of said ion exchange packing, wherein said packing inlet is fitted with said first flow through electrode and said packing outlet is fitted with said second flow through electrode.

26. The apparatus of claim 25 further comprising:
   (c) a source of flowing aqueous regenerant liquid in fluid communication with said packing inlet.

27. The apparatus of claim 26 further comprising:
   (d) a capillary chromatography column in fluid communication with said capillary tubing inlet.

28. The apparatus of claim 27 further comprising:
   (e) a flow-through detector in fluid communication with said capillary tubing outlet, and
   (f) a recycle conduit for directing recycled aqueous liquid from said detector to said ion exchange packing, whereby said aqueous regenerant liquid source comprises said recycled aqueous liquid.

29. The apparatus of claim 28 in which said aqueous liquid source further comprises an additional source of flowing aqueous liquid in addition to said recycled aqueous liquid.

30. The apparatus of claim 25 in which said ion exchange packing includes substrates with exchangeable ions comprising weakly acidic or weakly basic functional groups.

31. The apparatus of claim 25 in which an outer wall of said capillary tubing comprises exchangeable ions comprising weakly acidic or weakly basic functional groups.

32. The apparatus of claim 31 in which an inner wall of said capillary tubing comprises exchangeable ions comprising strongly acidic or strongly basic functional groups.

33. The apparatus of claim 31 in which said weakly acidic or weakly basic functional groups comprise moieties on polymers grafted to the outer wall of said tubing.

34. The apparatus of claim 25 in which said first electrode is disposed in an electrode chamber, said electrode chamber being out of contact with said flow-through ion exchange packing.

35. The apparatus of claim 34 in which said first electrode is disposed in an electrode chamber, said electrode chamber being out of contact with said flow-through ion exchange packing.

* * * * *